(12) United States Patent
Oda et al.

(10) Patent No.: US 12,403,240 B2
(45) Date of Patent: Sep. 2, 2025

(54) SYRINGE CONTROL ASSEMBLY

(71) Applicant: CareFusion 303, Inc., San Diego, CA (US)

(72) Inventors: Todd Oda, Torrance, CA (US); George Mansour, Diamond Bar, CA (US); Eugene Mason, La Habra Heights, CA (US); Tomas Frausto, Walnut, CA (US)

(73) Assignee: CAREFUSION 303, INC., San Diego, CA (US)

( * ) Notice: Subject to any disclaimer, the term of this patent is extended or adjusted under 35 U.S.C. 154(b) by 973 days.

(21) Appl. No.: 16/572,384

(22) Filed: Sep. 16, 2019

(65) Prior Publication Data

US 2021/0077711 A1  Mar. 18, 2021

(51) Int. Cl.
| | |
|---|---|
| *A61M 5/14* | (2006.01) |
| *A61M 5/00* | (2006.01) |
| *A61M 5/142* | (2006.01) |
| *A61M 39/24* | (2006.01) |

(52) U.S. Cl.
CPC .......... *A61M 5/1408* (2013.01); *A61M 5/008* (2013.01); *A61M 5/14236* (2013.01); *A61M 39/24* (2013.01); *A61M 2205/123* (2013.01)

(58) Field of Classification Search
CPC .. A61M 5/14236; A61M 5/1407–1409; A61M 5/008; A61M 5/178; A61M 5/142
See application file for complete search history.

(56) References Cited

U.S. PATENT DOCUMENTS

| | | | |
|---|---|---|---|
| 4,784,157 A | 11/1988 | Halls et al. | |
| 5,037,390 A | 8/1991 | Raines et al. | |
| 5,827,219 A * | 10/1998 | Uber, III | A61M 5/16827 604/30 |
| 6,471,674 B1 * | 10/2002 | Emig | A61M 5/1407 604/533 |
| 2003/0135388 A1 * | 7/2003 | Martucci | G06Q 10/087 705/2 |

(Continued)

FOREIGN PATENT DOCUMENTS

| | | |
|---|---|---|
| CN | 1589164 A | 3/2005 |
| CN | 201020077 Y | 2/2008 |

(Continued)

OTHER PUBLICATIONS

International Search Report and Written Opinion for Application No. PCT/US2020/050754, dated Nov. 24, 2020, 16 pages.

(Continued)

*Primary Examiner* — Kami A Bosworth
*Assistant Examiner* — Antarius S Daniel
(74) *Attorney, Agent, or Firm* — MASCHOFF BRENNAN (57) ABSTRACT

Syringe control assemblies are described herein. A syringe control assembly includes an assembly body, a first syringe, a second syringe, and a pump assembly. The first and second syringes are releasably coupled to a syringe mounting rack of the assembly body. The pump assembly includes a first pump unit and a second pump unit. Each pump unit is in fluid communication with each respective syringe. In a priming configuration, the first pump unit is configured to draw fluid flow from the first syringe cavity and the second pump unit is configured to pump fluid flow into the second syringe cavity.

20 Claims, 5 Drawing Sheets

(56) References Cited

U.S. PATENT DOCUMENTS

| | | | |
|---|---|---|---|
| 2004/0054320 A1* | 3/2004 | Kissinger | A61B 5/153 604/93.01 |
| 2005/0277912 A1* | 12/2005 | John | A61M 5/16827 604/890.1 |
| 2008/0167621 A1 | 7/2008 | Wagner et al. | |
| 2009/0306621 A1 | 12/2009 | Thome, Jr. et al. | |
| 2011/0130714 A1 | 6/2011 | Wells | |
| 2011/0196309 A1 | 8/2011 | Wells | |
| 2017/0281869 A1* | 10/2017 | Kai | B05B 7/2464 |
| 2019/0125971 A1* | 5/2019 | Bachrach | A61M 1/892 |

FOREIGN PATENT DOCUMENTS

| | | | |
|---|---|---|---|
| CN | 101784295 A | 7/2010 |
| CN | 105073157 A | 11/2015 |
| CN | 107684644 A | 2/2018 |
| EP | 2448614 A2 | 5/2012 |
| JP | S63290578 A | 11/1988 |
| JP | 2008535575 A | 9/2008 |
| JP | 2010063767 A | 3/2010 |
| JP | 2010512880 A | 4/2010 |
| JP | 2014527881 A | 10/2014 |
| JP | 2015134171 A | 7/2015 |
| WO | WO-2005110007 A2 | 11/2005 |
| WO | WO-2008077573 A2 | 7/2008 |
| WO | WO-2009076429 A2 | 6/2009 |
| WO | WO-2010039662 A2 | 4/2010 |
| WO | WO-2017064656 A1 | 4/2017 |
| WO | WO-2018144369 A1 | 8/2018 |

OTHER PUBLICATIONS

Chinese Office Action for Application No. 202080079487.0, dated Jan. 3, 2024, 29 pages including translation.

Chinese Office Action for Application No. 202080079487.0, dated Aug. 31, 2024, 20 pages including translation.

Japanese Office Action for Application No. 2022-516602, dated Jul. 23, 2024, 11 pages including translation.

Chinese Notification to Grant for Application No. 202080079487.0, dated Nov. 9, 2024, 7 pages including translation.

Indian Office Action for Application No. 202217016776, dated Dec. 18, 2024, 7 pages.

Japanese Office Action for Application No. 2022-516602, dated Nov. 5, 2024, 3 pages including translation.

* cited by examiner

SYRINGE CONTROL ASSEMBLY

FIELD OF THE INVENTION

The present disclosure generally relates to medication delivery systems, and, in particular, to syringe control assemblies.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, a syringe. Certain configurations of IV sets may have extended lengths of tubing, for example, in excess of 6 feet. Additionally, tubing may be primed with saline prior to the infusion of a liquid medication.

In some applications, during the use of IV catheters, saline from the priming process may be delivered to patient before the liquid medication is delivered to the patient.

SUMMARY

The disclosed subject matter relates to syringe control assemblies. In certain embodiments, a syringe control assembly is disclosed that comprises an assembly body comprising a syringe mounting rack; a first syringe releasably coupled to the syringe mounting rack, the first syringe comprising a first syringe body defining a first syringe cavity and a first syringe port, wherein the first syringe port is in fluid communication with the first syringe cavity; a second syringe releasably coupled to the syringe mounting rack, the second syringe comprising a second syringe body defining a second syringe cavity and a second syringe port, wherein the second syringe port is in fluid communication with the second syringe cavity; and a pump assembly coupled to the assembly body, the pump assembly comprising: a first pump unit in fluid communication with the first syringe port via a first pump tubing; and a second pump unit in fluid communication with the second syringe port via a second pump tubing, wherein in a priming configuration the first pump unit is configured to draw fluid flow from the first syringe cavity and the second pump unit is configured to pump fluid flow into the second syringe cavity.

In certain embodiments, a method to deliver medication is disclosed that comprises pumping medication from a first medication syringe into a delivery flow path of a tubing; and pumping medical fluid from a return flow path of the tubing into a return syringe.

In certain embodiments, a medication delivery system is disclosed that comprises a syringe control assembly, comprising; an assembly body comprising a syringe mounting rack; a first syringe releasably coupled to the syringe mounting rack, the first syringe comprising a first syringe body defining a first syringe cavity and a first syringe port, wherein the first syringe port is in fluid communication with the first syringe cavity; a second syringe releasably coupled to the syringe mounting rack, the second syringe comprising a second syringe body defining a second syringe cavity and a second syringe port, wherein the second syringe port is in fluid communication with the second syringe cavity; and a pump assembly coupled to the assembly body, the pump assembly comprising: a first pump unit in fluid communication with the first syringe port via a first pump tubing; and a second pump unit in fluid communication with the second syringe port via a second pump tubing; and a tubing defining a delivery flow path and a return flow path, wherein in a priming configuration the delivery flow path is in fluid communication with the first pump unit to pump fluid flow from the first syringe cavity though the delivery flow path and the return flow path is in fluid communication with the second pump unit to pump fluid flow from the return flow path into the second syringe cavity.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed syringe control assembly incorporates syringes with respective pump units to control the fluid flow of medication and saline. The syringe control assembly can control the delivery and return flow of medical fluids such as medication and saline. By controlling the fluid flow medical fluids, the priming and delivery of medication and other medical fluids can be simplified.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to the administration of medical fluid using the disclosed syringe control assembly, it is to be understood that this description is only an example of usage and does not limit the scope of the claims. Various aspects of the disclosed syringe control assembly may be used in any application where it is desirable to provide for the administration of medical fluids.

The disclosed syringe control assembly overcomes several challenges discovered with respect to certain conventional syringes. One challenge with certain conventional syringes is that syringes may deliver excess medical fluid, such as saline, to patients. Further, conventional syringes may require manual advancing and retraction in sequence. Because excess medical fluid may delay the delivery of medical fluids and may not be tolerated by fluid restricted patients, such as premature babies, and because manual operation of conventional syringes may be subject to error, the use conventional syringes is undesirable.

Therefore, in accordance with the present disclosure, it is advantageous to provide a syringe control assembly as described herein that eliminates or substantially reduces delivering excess medical fluid to a patient and simplifies the operation of the syringes. The disclosed syringe assembly provides pump units that permit simplified operation while reducing excess medical fluid delivered to the patient.

An example of a syringe control assembly that prevents delivery of excess medical fluid is now described.

Figure 1:
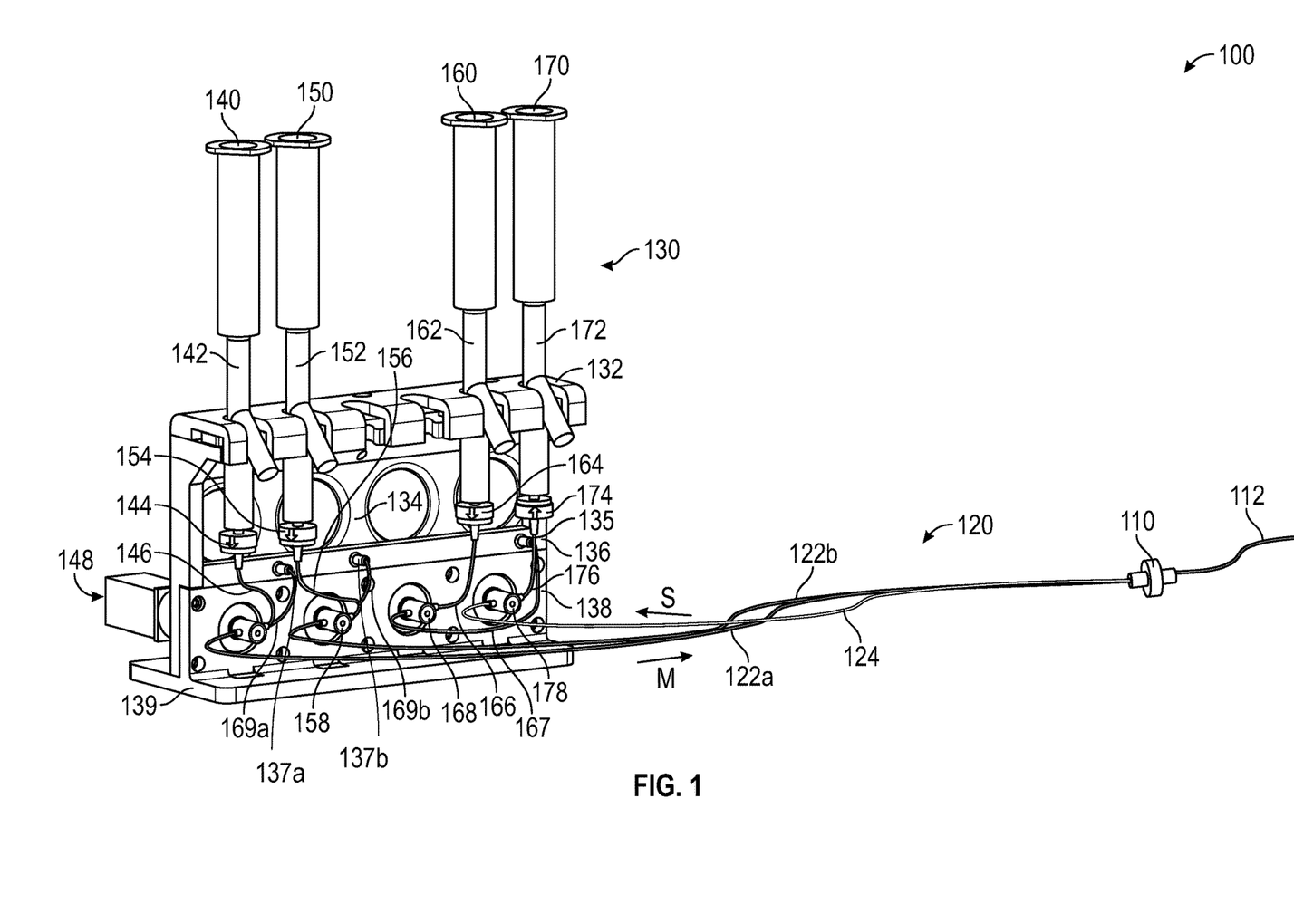
FIG. 1 is a perspective view of a medication delivery system in a priming configuration, in accordance with various aspects of the present disclosure.

FIG. 1 is a perspective view of a medication delivery system 100 in a priming configuration, in accordance with various aspects of the present disclosure. In the illustrated example, the medication delivery system 100 delivers medication from the syringe control assembly 130 to the patient via catheter 112 without delivering excess fluid, such as saline, used to prime the medication delivery system 100.

Optionally, prior to administering or priming medication, delivery flow path 122a of the multi-lumen tubing 120 can be primed with saline to remove any air or trapped gasses within the delivery flow path 122a. Saline can be advanced from the syringe control assembly 130, through the delivery flow path 122a and to the valve 110.

The saline from the delivery flow path 122a of the multi-lumen tubing 120 can be received within the valve 110. In a priming configuration, the valve 110 can prevent saline from the delivery flow path 122a from entering the catheter 112 and can instead direct the saline through the return flow path 124 to allow primed saline to be returned to the syringe control assembly 130. Similarly, the delivery flow path 122b can be primed with saline.

In the illustrated example, the syringe control assembly 130 advances medication within the delivery flow path 122a to prime the delivery flow path 122a. Advantageously, by priming the delivery flow path 122a with medication, the medication can be delivered to the patient via the catheter 112 proximal to the patient with less delay and without delivering the saline used to prime the delivery flow path 122a of the multi-lumen tubing 120.

To introduce medication into the delivery flow path 122a, the syringe control assembly 130 includes a first medication pump unit 148 to pump or draw medication from the first medication syringe 140 via tubing 146 and pump or direct the medication through the delivery flow path 122a.

In the illustrated embodiment, the first medication administered by the syringe control assembly 130 is stored within the first medication syringe 140. Optionally, the first medication syringe 140 is disposable. The first medication syringe 140 stores first medication within a cavity 142 defined within the syringe body. The first medication from the cavity 142 is drawn through the port 144 by the first medication pump unit 148. The first medication is directed from the port 164 to the first medication pump unit 148 via tubing 146. In some embodiments, the port 144 can include a check valve to prevent the backflow of the first medication, saline, or other medical fluids into the cavity 142 of the first medication syringe 140. As illustrated, the first medication syringe 140 can be releasably coupled to a syringe mounting rack 132. Optionally, the syringe mounting rack 132 can include quick release mounting points to allow for rapid attachment, detachment, or exchange of the first medication syringe 140 or other components. The syringe mounting rack 132 can be coupled to the assembly body 134.

In some embodiments, the first medication pump unit 148 includes a pump to impart fluid pressure to provide fluid flow to the medication from the first medication syringe 140. As described herein, various types of pumps can be utilized. Similarly, various types of motors or actuators can be used to actuate the pump. As shown, the first medication pump unit 148 can be coupled to the pump assembly 138. The pump assembly 138 can be coupled to the assembly body 134. Optionally, the pump assembly 138 can form a portion of the base 139 of the syringe control assembly 130.

In some embodiments, operational parameters of the first medication pump unit 148 such as the amount of fluid flow and/or the fluid pressure provided can be adjusted either before or during operation. Optionally, in some embodiments, the first medication pump unit 148 can function as an on/off valve, permitting flow therethrough when the pump portion is active and preventing flow (including backflow and cross-flow) therethrough when the pump portion is inactive.

Optionally, the first medication pump unit 148 can be configured to pump or dispense a desired volume of medication from the first medication syringe 140 into the delivery flow path 122a of the multi-lumen tubing 120 that is equivalent to the volume of the delivery flow path 122a. In other words, the first medication pump unit 148 can be operated to fill the volume of the delivery flow path 122a up to the valve 110 to prime the delivery flow path 122a with the first medication to prime the first medication for administration via the catheter 112.

In some embodiments, the priming of the first medication in to the delivery flow path 122a can be controlled, automated, or otherwise simplified. For example, the operation of the first medication pump unit 148 can be controlled or automated to be started, stopped, or sequenced to allow a desired volume of the first medication to be introduced into the delivery flow path 122a.

Optionally, the syringe control assembly 130 includes a second medication syringe 150 to facilitate the administration of a secondary medication or additional volume of the first medication. As described herein, the secondary medication can be administered simultaneously with the first medication or can be administered sequentially. Similarly, the secondary medication can be advanced within the delivery flow path 122b to prime the delivery flow path 122b.

To introduce medication into the delivery flow path 122b, the syringe control assembly 130 includes a second medication pump unit 158 to pump or draw medication from the second medication syringe 150 via tubing 156 and pump or direct the medication through the delivery flow path 122b.

In the illustrated embodiment, the second medication administered by the syringe control assembly 130 is stored within the second medication syringe 150. Optionally, the second medication syringe 150 is disposable. The second medication syringe 150 stores second medication within a cavity 152 defined within the syringe body. The second medication from the cavity 152 is drawn through the port 154 by the second medication pump unit 158. The second medication is directed from the port 154 to the second medication pump unit 158 via tubing 156. In some embodiments, the port 154 can include a check valve to prevent the backflow of the second medication, saline, or other medical fluids into the cavity 152 of the second medication syringe 150. As illustrated, the second medication syringe 150 can be releasably coupled to a syringe mounting rack 132.

In some embodiments, the second medication pump unit 158 includes a pump to impart fluid pressure to provide fluid flow to the medication from the second medication syringe 150. As shown, the second medication pump unit 158 can be coupled to the pump assembly 138.

In some embodiments, operational parameters of the second medication pump unit 158 such as the amount of fluid flow and/or the fluid pressure provided can be adjusted either before or during operation. Optionally, in some embodiments, the second medication pump unit 158 can function as an on/off valve, permitting flow therethrough when the pump portion is active and preventing flow (including backflow and cross-flow) therethrough when the pump portion is inactive.

Optionally, the second medication pump unit 158 can be configured to pump or dispense a desired volume of medication from the second medication syringe 150 into the delivery flow path 122b of the multi-lumen tubing 120 that is equivalent to the volume of the delivery flow path 122b. In other words, the second medication pump unit 158 can be operated to fill the volume of the delivery flow path 122b up to the valve 110 to prime the delivery flow path 122b with the second medication to prime the second medication for administration via the catheter 112.

In some embodiments, the priming of the second medication in to the delivery flow path 122b can be controlled, automated, or otherwise simplified. For example, the operation of the second medication pump unit 158 can be controlled or automated to be started, stopped, or sequenced to allow a desired volume of the second medication to be introduced into the delivery flow path 122b. As can be appreciated, the second medication pump unit 158 can be configured to prime the delivery flow path 122b sequentially or simultaneously with the first medication pump unit 148.

As illustrated, as the first medication is introduced into the delivery flow path 122a of the multi-lumen tubing 120, any saline or other medical fluids previous primed through the delivery flow path 122a are displaced. Similarly, as the second medication is introduced into the delivery flow path 122b of the multi-lumen tubing 120, any saline or other medical fluids previous primed through the delivery flow path 122b are displaced. The displaced fluids are directed by the valve 110 into the return flow path 124. In some applications, pressure from the first medication pump unit 148 and/or the second medication pump unit 158 may be sufficient to flow displaced medical fluids to the syringe control assembly 130. In some embodiments, displaced fluids from the return flow path 124 can be drawn or pumped by the syringe control assembly 130.

For example, to facilitate the flow of displaced medical fluids from the return flow path 124, the syringe control assembly 130 includes a return pump unit 178 to pump or draw displaced fluids from the return flow path 124 and pump or direct the fluids to a return syringe 170 via tubing 176.

In the illustrated embodiment, the return pump unit 178 includes a pump to impart fluid pressure to displaced fluids within the return flow path 124. As shown, the return pump unit 178 can be coupled to the pump assembly 138.

In some embodiments, operational parameters of the return pump unit 178 such as the amount of fluid flow and/or the fluid pressure provided can be adjusted either before or during operation. Optionally, in some embodiments, the return pump unit 178 can function as an on/off valve, permitting flow therethrough when the pump portion is active and preventing flow (including backflow and cross-flow) therethrough when the pump portion is inactive.

Optionally, the return pump unit 178 can be configured to facilitate priming operations. For example, the return pump unit 178 can be configured to pump or dispense a volume of displaced fluids corresponding to the amount of medication or other fluid introduced during priming. In other embodiments, the return pump unit 178 can operate simultaneously during the priming operation of the first medication pump unit 148 and/or the second medication pump unit 158.

In some embodiments, the return pump unit 178 can be controlled to start, stop, or be sequenced cooperatively with the first medication pump unit 148 and/or the second medication pump unit 158 until the priming operation is completed.

In the illustrated embodiment, the displaced fluids received by the syringe control assembly 130 are stored within the return syringe 170. Optionally, the return syringe 170 is disposable. The return syringe 170 stores returned fluids within a cavity 172 defined within the return syringe body. The returned fluids can be introduced into the cavity 172 by a port 174 in fluid communication with the return pump unit 178. Tubing 176 can direct flow from the return pump unit 178 to the port 174. In some embodiments, the port 174 can include a check valve to prevent the outflow of the returned fluids from the cavity 172. As illustrated, the return syringe 170 can be releasably coupled to the syringe mounting rack 132.

Figure 2:
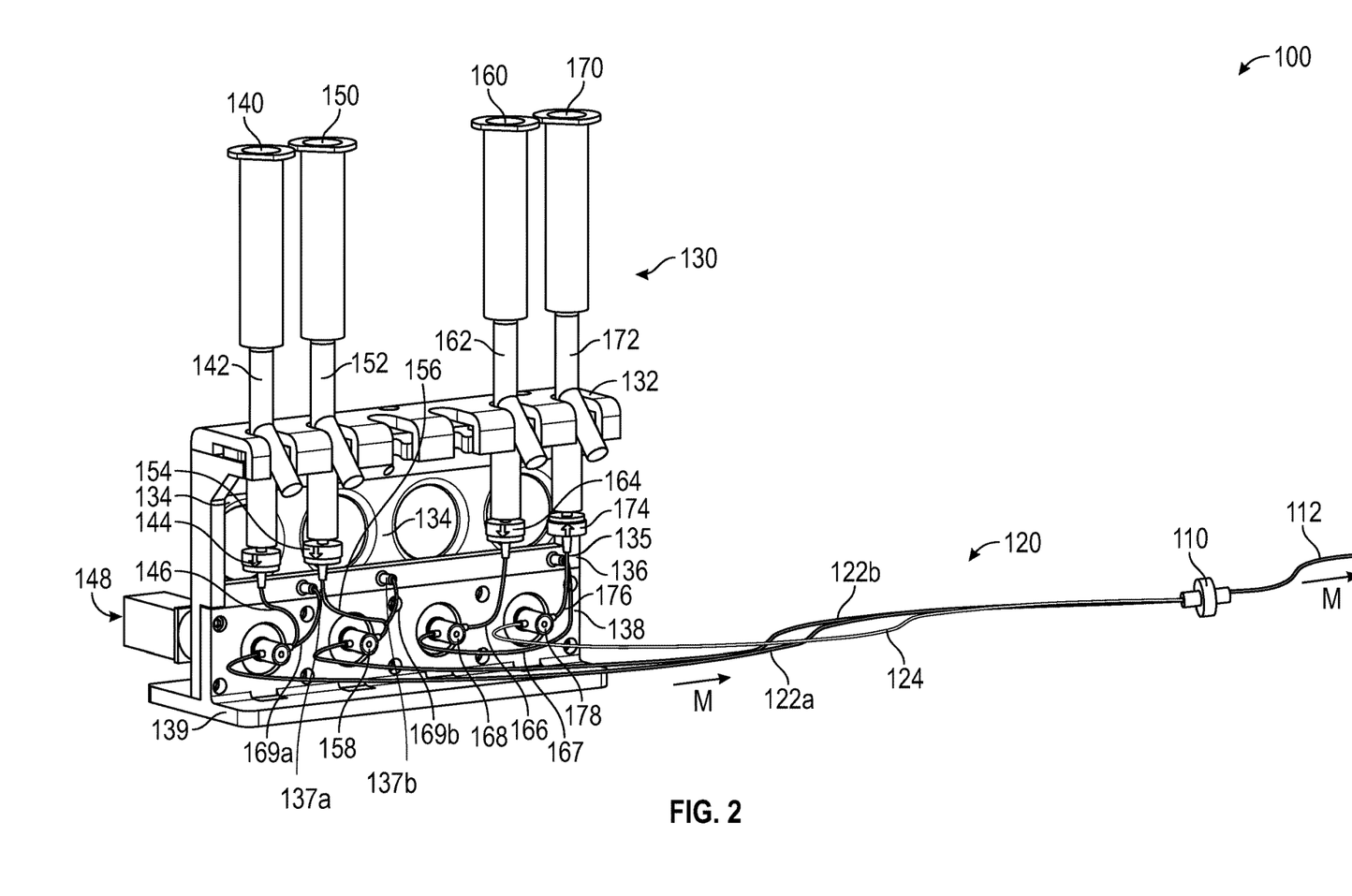
FIG. 2 is a perspective view of the medication delivery system of FIG. 1 in a delivery configuration, in accordance with various aspects of the present disclosure.

FIG. 2 is a perspective view of the medication delivery system 100 of FIG. 1 in a delivery configuration, in accordance with various aspects of the present disclosure. In the illustrated example, the syringe control assembly 130 dispenses medication to the patient through the catheter 112.

During the delivery operation, the first medication pump unit 148 is activated to deliver the first medication from the first medication syringe 140 into the primed delivery flow path 122a. As the first medication is delivered into the delivery flow path 122a, the valve 110 is actuated to permit the flow of medication from the delivery flow path 122a to the patient via the catheter 112. In some embodiments, the valve 110 is actuated by fluid pressure or other actuation mechanisms. Optionally, the valve 110 can be located proximally to the patient to minimize the length of the catheter 112, to reduce the amount of saline administered to the patient and to reduce the delivery time for the medication.

Optionally, the second medication pump unit 158 is activated to deliver the second medication from the second medication syringe 150 into the primed delivery flow path 122b. Similarly, the valve 110 can permit the flow of medication from the delivery flow path 122b to the patient via the catheter 112. In some embodiments, the second medication can be delivered to the patient sequentially after the first medication. In some applications, the second medication can be delivered simultaneously with the first medication wherein the first medication and the second medication flow combine at the valve 110 to be administered to the patient via the catheter 112.

Figure 3:
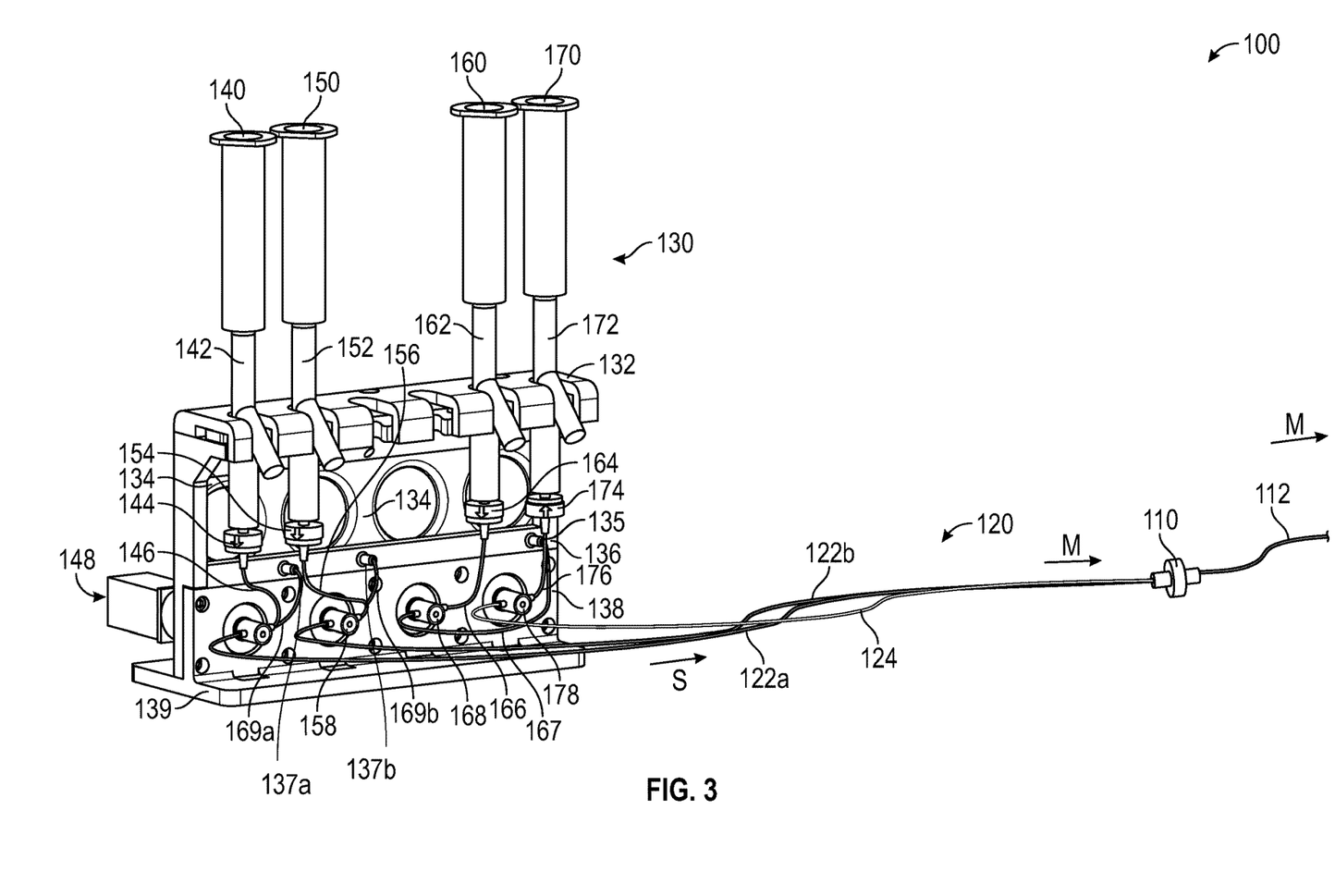
FIG. 3 is a perspective view of the medication delivery system of FIG. 1 in a pushing configuration, in accordance with various aspects of the present disclosure.

FIG. 3 is a perspective view of the medication delivery system 100 of FIG. 1 in a pushing configuration, in accordance with various aspects of the present disclosure. In the illustrated example, the syringe control assembly 130 can advance saline through the delivery flow path 122a and/or delivery flow path 122b of the multi-lumen tubing 120 to advance the remaining medication to the patient via the catheter 112.

For example, after the first medication is expelled from the syringe control assembly 130, the first medication may remain in the volume of the delivery flow path 122a. To ensure that the medication is fully delivered to the patient in the desired dosage, the syringe control assembly 130 can be utilized to administer a saline "push" to continue to advance the medication through the delivery flow path 122a after the medication within the first medication syringe 140 is exhausted. In some applications, saline can be administered through the delivery flow path 122a until the medication is fully administered to the patient. Similarly, saline can be administered through the delivery flow path 122b until medication is fully administered to the patient.

In some embodiments, the syringe control assembly 130 includes a saline syringe 160 to facilitate the administration of a saline push within the delivery flow path 122a and/or delivery flow path 122b to advance any remaining medication therein.

To introduce saline into the delivery flow path 122a and/or delivery flow path 122b, the syringe control assembly 130 includes a saline pump unit 168 to pump or draw saline from the saline syringe 160 via tubing 166 and pump or direct the saline through the delivery flow path 122a and/or the delivery flow path 122b.

In the illustrated embodiment, saline administered by the syringe control assembly 130 is stored within the saline syringe 160. Optionally, the saline syringe 160 is disposable. The saline syringe 160 stores saline within a cavity 162 defined within the syringe body. The saline from the cavity 162 is drawn through the port 164 by the saline pump unit 168. The saline is directed from the port 164 to the saline pump unit 168 via tubing 166. In some embodiments, the port 164 can include a check valve to prevent the backflow of the medication, saline, or other medical fluids into the cavity 162 of the saline syringe 160. As illustrated, the saline syringe 160 can be releasably coupled to a syringe mounting rack 132.

In some embodiments, the saline pump unit 168 includes a pump to impart fluid pressure to provide fluid flow to the medication from the saline syringe 160. As shown, the saline pump unit 168 can be coupled to the pump assembly 138.

In some embodiments, operational parameters of the saline pump unit 168 such as the amount of fluid flow and/or the fluid pressure provided can be adjusted either before or during operation. In some embodiments, the saline pump unit 168 may be in fluid communication with, and operated simultaneously as the first medication pump unit 148 and/or the second medication pump unit 158. Optionally, in some embodiments, the saline pump unit 168 can function as an on/off valve, permitting flow therethrough when the pump portion is active and preventing flow (including backflow and cross-flow) therethrough when the pump portion is inactive.

Optionally, the saline pump unit 168 can be configured to pump or dispense a desired volume of saline from the saline syringe 160 into the delivery flow path 122a and/or the delivery flow path 122b of the multi-lumen tubing 120 that is sufficient to push or administer the desired amount of medication to the patient. In some embodiments, the pushing of the medication in the delivery flow path 122a and/or the delivery flow path 122b can be controlled, automated, or otherwise simplified. For example, the operation of the saline pump unit 168 can be controlled or automated to be started, stopped, or sequenced to allow a desired volume of the saline to be introduced into the delivery flow path 122a and/or the delivery flow path 122b.

In some embodiments, the saline pump unit 168 directs saline from the saline syringe 160 to a saline manifold 136 to distribute the saline to the delivery flow path 122a and/or the delivery flow path 122b. In some embodiments, the saline manifold 136 can be coupled to or formed with the assembly body 134. Optionally, the saline manifold can be disposed between the syringe mounting rack 132 and the pump assembly 138. As illustrated, the saline manifold 136 receives saline flow from the saline pump unit 168 at the manifold inlet 135 via the manifold inlet tubing 167. Saline flow within the saline manifold 136 is directed to the first medication pump unit 148 by a first manifold outlet 137a via a manifold outlet tubing 169a and to the second medication pump unit 158 by a second manifold outlet 137b via a manifold outlet tubing 169b. As described herein, the first medication pump unit 148 and the second medication pump unit 158 can permit or prevent flow therethrough.

For example, to provide a saline push of the medication within the delivery flow path 122a, the first medication pump unit 148 may operate to permit saline flow from the saline manifold 136 to the delivery flow path 122a, advancing medication therethrough. To prevent the backflow of saline, the saline pump unit 168 may be overdriven or otherwise configured to provide a greater fluid output than the first medication pump unit 148. Optionally, to provide a saline push of the medication within the delivery flow path 122b, the second medication pump unit 158 may operate to permit saline flow from the saline manifold 136 to the delivery flow path, advancing the medication therethrough. Similarly, to prevent the backflow of saline, the saline pump unit 168 may be overdriven or otherwise configured to provide a greater fluid output than the second medication pump unit 158.

Figure 4:
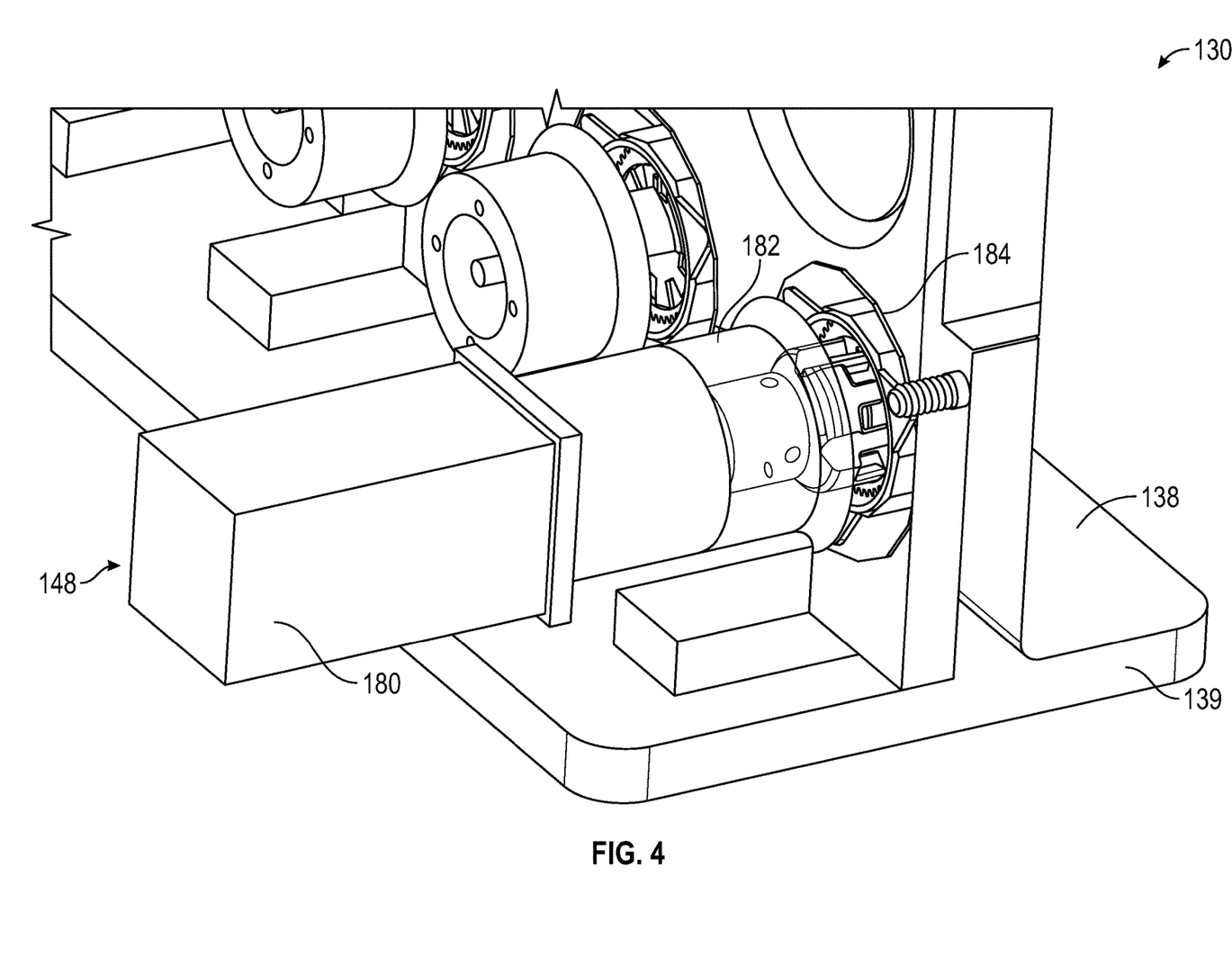
FIG. 4 is a reverse perspective view of the syringe control assembly of FIG. 1, in accordance with various aspects of the present disclosure.
Figure 5:
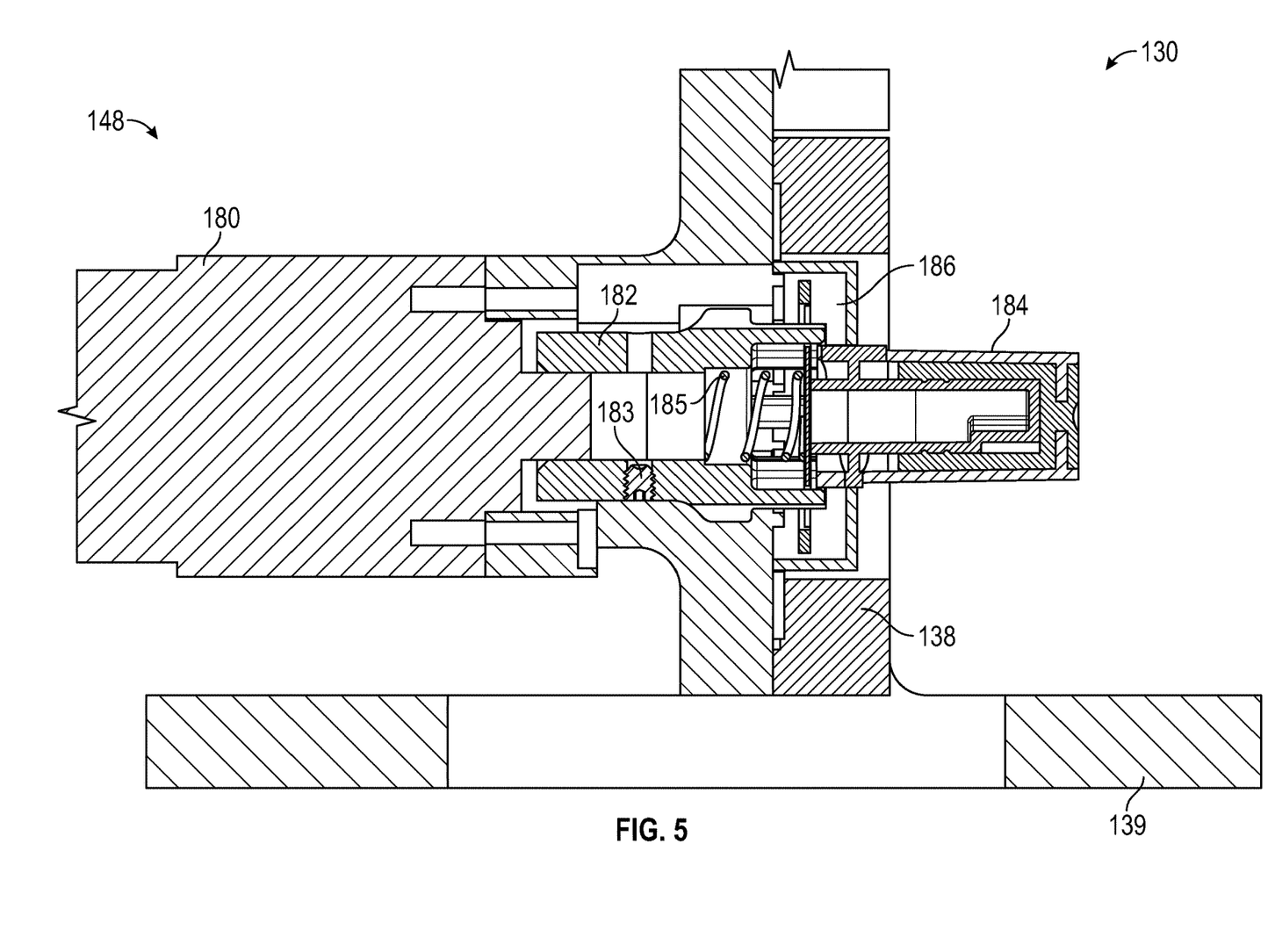
FIG. 5 is a partial cross sectional view of the syringe control assembly of FIG. 1, in accordance with various aspects of the present disclosure.

FIG. 4 is a reverse perspective view of the syringe control assembly 130 of FIG. 1, in accordance with various aspects of the present disclosure. FIG. 5 is a partial cross sectional view of the syringe control assembly 130 of FIG. 1, in accordance with various aspects of the present disclosure. In some embodiments, the syringe control assembly 130 can include a first medication pump unit 148, a second medication pump unit 158, a saline pump unit 168, and/or a return pump unit 178 to control and direct fluid flow for the medication delivery system 100. While FIGS. 4 and 5 depict the first medication pump unit 148, features described with respect to embodiments of the first medication pump unit 148 can be included with respect to embodiments of a second medication pump unit 158, a saline pump unit 168, and/or a return pump unit 178.

As illustrated, the first medication pump unit 148 includes a rotary pump 184 to pressurize and provide fluid flow for medical fluids. Optionally, the rotary pump 184 can be disposable. During operation, the pump cavity 186 can receive fluid flow from the first medication syringe 140. When actuated, the rotary pump 184 can pressurize fluid within the pump cavity 186 to provide fluid flow.

The rotary pump 184 can be rotated by a motor 180. The shaft of the motor 180 can be coupled to the rotary pump 184 to transmit rotation with a coupling 182. The coupling 182 can be secured with a set screw 183. In some embodiments, the coupling 182 can be biased with a spring 185 to provide a desired preload to the connection between the rotary pump 184 and the motor 180. In some embodiments, the motor 180 is a stepper motor to allow for control of the position of the rotary pump 184 and allow for precise dispensing of medication.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A syringe control assembly, comprising:
   an assembly body comprising a syringe mounting rack;
   a first syringe releasably coupled to the syringe mounting rack, the first syringe comprising a first syringe body defining a first syringe cavity and a first syringe port, wherein the first syringe port is in fluid communication with the first syringe cavity;
   a second syringe releasably coupled to the syringe mounting rack, the second syringe comprising a second syringe body defining a second syringe cavity and a second syringe port, wherein the second syringe port is in fluid communication with the second syringe cavity; and
   a pump assembly coupled to the assembly body, the pump assembly comprising:
      a first pump unit in fluid communication with the first syringe port via a first pump tubing, wherein the first pump unit comprises:
         a rotary pump comprising a pump cavity in fluid communication with the first syringe port; and a motor coupled to the pump, wherein the motor is configured to rotate a portion of the rotary pump; and a second pump unit in fluid communication with the second syringe port via a second pump tubing, wherein in a priming configuration the first syringe cavity and the second syringe cavity are in fluid communication and the first pump unit is configured to draw fluid flow from the first syringe cavity toward a catheter and the second pump unit is configured to pump fluid flow from the first syringe cavity toward the second syringe cavity, and a valve, wherein a first portion of the valve is directly coupled to a terminal end of a delivery flow path from the first syringe cavity and a terminal end of a return flow path to the second syringe cavity, and a second portion of the valve is directly coupled to a terminal end of the catheter, wherein the valve is configured to prevent fluid flow from the first syringe cavity from entering the catheter and to direct fluid flow from the first syringe cavity through the valve and toward the second syringe cavity in the priming configuration.

2. The syringe control assembly of claim 1, further comprising:

a fluid manifold comprising a manifold inlet and a manifold outlet, wherein the manifold inlet and the manifold outlet are in fluid communication and the manifold outlet is in fluid communication with the first pump unit; and a third syringe releasably coupled to the syringe mounting rack, the third syringe comprising a third syringe body defining a third syringe cavity and a third syringe port, wherein the third syringe port is in fluid communication with the third syringe cavity, wherein the pump assembly further comprises:

a third pump unit in fluid communication with the third syringe port via a third pump tubing, wherein in a pushing configuration the third pump unit is configured to direct fluid flow from the third syringe cavity into the manifold inlet and the first pump unit is configured to receive fluid flow from the first syringe cavity and the manifold outlet.

3. The syringe control assembly of claim 2, wherein the fluid manifold is disposed between the syringe mounting rack and the pump assembly.

4. The syringe control assembly of claim 1, further comprising:

a fourth syringe releasably coupled to the syringe mounting rack, the fourth syringe comprising a fourth syringe body defining a fourth syringe cavity and a fourth syringe port, wherein the fourth syringe port is in fluid communication with the fourth syringe cavity, wherein the pump assembly further comprises:

a fourth pump unit in fluid communication with the fourth syringe port via a fourth pump tubing, wherein the fourth pump unit is configured to draw fluid flow from the fourth syringe cavity.

5. The syringe control assembly of claim 4, wherein in a simultaneous delivery configuration the fourth pump unit is configured to draw fluid flow from the fourth syringe cavity while the first pump unit is configured to draw fluid flow from the first syringe cavity.

6. The syringe control assembly of claim 4, wherein in a sequential delivery configuration the fourth pump unit is configured to draw fluid flow from the fourth syringe cavity after the first pump unit is configured to draw fluid flow from the first syringe cavity.

7. The syringe control assembly of claim 1, wherein first syringe comprises a first check valve in fluid communication with the first syringe port, wherein the first check valve prevents backflow into the first syringe cavity.

8. The syringe control assembly of claim 1, wherein second syringe comprises a second check valve in fluid communication with the second syringe port, wherein the second check valve prevents flow out of the second syringe cavity.

9. The syringe control assembly of claim 1, wherein the valve is configured to provide fluid communication between the first syringe cavity and the second syringe cavity in the priming configuration.

10. The syringe control assembly of claim 1, wherein the valve is configured to prevent fluid flow from the first syringe cavity via a delivery flow path from entering the catheter in the priming configuration.

11. The syringe control assembly of claim 10, wherein the valve is configured to direct fluid flow from the first syringe cavity toward the second syringe cavity via a return flow path in the priming configuration.

12. A method to deliver medication, the method comprising:

pumping medication from a first medication syringe into a delivery flow path of a tubing and toward a catheter via a rotary pump in fluid communication with the first medication syringe;

pumping medical fluid from the first medication syringe via a return flow path of the tubing toward a return syringe in fluid communication with the first medication syringe in a priming configuration;

preventing medical fluid from the delivery flow path from entering the catheter via a valve, wherein a first portion of the valve is directly coupled to a terminal end of the delivery flow path and a terminal end of the return flow path, and a second portion of the valve is directly coupled to a terminal end of the catheter; and directing medical fluid from the delivery flow path to the return flow path through the valve.

13. The method of claim 12, further comprising:
pumping medical fluid and pumping medication from the first medication syringe simultaneously.

14. The method of claim 12, further comprising:
pumping saline from a saline syringe into the delivery flow path of the tubing after pumping medication from the first medication syringe.

15. The method of claim 12, further comprising:
pumping medication from a second medication syringe into the delivery flow path of the tubing.

16. The method of claim 15, further comprising:
pumping medication from the first medication syringe and the second medication syringe simultaneously.

17. The method of claim 15, further comprising:
pumping medication from the first medication syringe and the second medication syringe sequentially.

18. A medication delivery system, comprising:
a syringe control assembly, comprising:
an assembly body comprising a syringe mounting rack;
a first syringe releasably coupled to the syringe mounting rack, the first syringe comprising a first syringe body defining a first syringe cavity and a first syringe port, wherein the first syringe port is in fluid communication with the first syringe cavity;
a second syringe releasably coupled to the syringe mounting rack, the second syringe comprising a second syringe body defining a second syringe cavity and a second syringe port, wherein the second syringe port is in fluid communication with the second syringe cavity; and a pump assembly coupled to the assembly body, the pump assembly comprising:
  a first pump unit in fluid communication with the first syringe port via a first pump tubing, wherein the first pump unit comprises:
    a rotary pump comprising a pump cavity in fluid communication with the first syringe port; and
    a motor coupled to the pump, wherein the motor is configured to rotate a portion of the rotary pump; and
  a second pump unit in fluid communication with the second syringe port via a second pump tubing;

a tubing defining a delivery flow path and a return flow path, wherein in a priming configuration the delivery flow path and the return flow path are in fluid communication, and the delivery flow path is in fluid communication with the first pump unit to pump fluid flow from the first syringe cavity though the delivery flow path toward a catheter and the return flow path is in fluid communication with the second pump unit to pump fluid flow from the first syringe cavity via the deliver flow path toward the return flow path and the second syringe cavity; and a valve, wherein a first portion of the valve is directly coupled to a terminal end of the delivery flow path and a terminal end of the return flow path, and a second portion of the valve is directly coupled to a terminal end of the catheter, wherein the valve is configured to prevent fluid flow from delivery flow path from entering the catheter and to direct fluid flow from the delivery flow path through the valve and to the return flow path in the priming configuration.

19. The medication delivery system of claim 18, the syringe control assembly further comprising:

a fluid manifold comprising a manifold inlet and a manifold outlet, wherein the manifold inlet and the manifold outlet are in fluid communication and the manifold outlet is in fluid communication with the first pump unit; and a third syringe releasably coupled to the syringe mounting rack, the third syringe comprising a third syringe body defining a third syringe cavity and a third syringe port, wherein the third syringe port is in fluid communication with the third syringe cavity, wherein the pump assembly further comprises:
  a third pump unit in fluid communication with the third syringe port via a third pump tubing, wherein in a pushing configuration, the third pump unit is configured to direct fluid flow from the third syringe cavity into the manifold inlet and the first pump unit is configured to pump fluid flow from the first syringe cavity and the manifold outlet through the delivery flow path.

20. The medication delivery system of claim 18, the syringe control assembly further comprising:

a fourth syringe releasably coupled to the syringe mounting rack, the fourth syringe comprising a fourth syringe body defining a fourth syringe cavity and a fourth syringe port, wherein the fourth syringe port is in fluid communication with the fourth syringe cavity, wherein the pump assembly further comprises:
  a fourth pump unit in fluid communication with the fourth syringe port via a fourth pump tubing, wherein in a secondary medication delivery configuration, the delivery flow path is in fluid communication with the first pump unit and the fourth pump unit to pump fluid flow from the fourth syringe cavity though a second delivery flow path of the tubing.

* * * * *